(12) United States Patent
Enrico et al.

(10) Patent No.: US 6,610,686 B1
(45) Date of Patent: Aug. 26, 2003

(54) USE OF PIRENOXINE FOR THE PROTECTION OF CORNEAL TISSUES IN PHOTOKERACTOMY

(75) Inventors: Boldrini Enrico, Pisa (IT); Ciuffi Mario, Florence (IT)

(73) Assignee: Ausimont S.p.A., Milan (IT)

( * ) Notice: Subject to any disclaimer, the term of this patent is extended or adjusted under 35 U.S.C. 154(b) by 0 days.

(21) Appl. No.: 09/936,597

(22) PCT Filed: Mar. 13, 2000

(86) PCT No.: PCT/IT00/00081

§ 371 (c)(1),
(2), (4) Date: Nov. 15, 2001

(87) PCT Pub. No.: WO00/54757

PCT Pub. Date: Sep. 21, 2000

(30) Foreign Application Priority Data

Mar. 17, 1999 (IT) ......................................... RM99A0166

(51) Int. Cl.⁷ ............................................. A61K 31/533

(52) U.S. Cl. ................................. 514/229.8; 514/232.8; 514/912

(58) Field of Search .......................... 514/229.8, 232.8, 514/912

(56) References Cited

FOREIGN PATENT DOCUMENTS

WO          0885612 A1 * 12/1998

* cited by examiner

*Primary Examiner*—Zohreh Fay
(74) *Attorney, Agent, or Firm*—Bryan Cave LLP

(57) ABSTRACT

Pirenoxine or 1-hydroxy-5-oxo-5H-pyrido-[3,2a]-phenoxazin-3-carboxylic acid, also called pirfenossone and already used as anti-cataract agent, in the form of a pharmaceutically acceptable salt thereof, if desired, is used for the protection of the corneal tissue in photokeratectomy interventions, as cornea photoablation using excimer laser, for both refractive and therapeutic purpose. In fact pirenoxine is able to inhibit, in the cornea, the oxidative phenomena determined by reactive oxygen species (ROS) which are produced within the tissues following the laser irradiation.

9 Claims, 3 Drawing Sheets

USE OF PIRENOXINE FOR THE PROTECTION OF CORNEAL TISSUES IN PHOTOKERACTOMY

Figure 1:
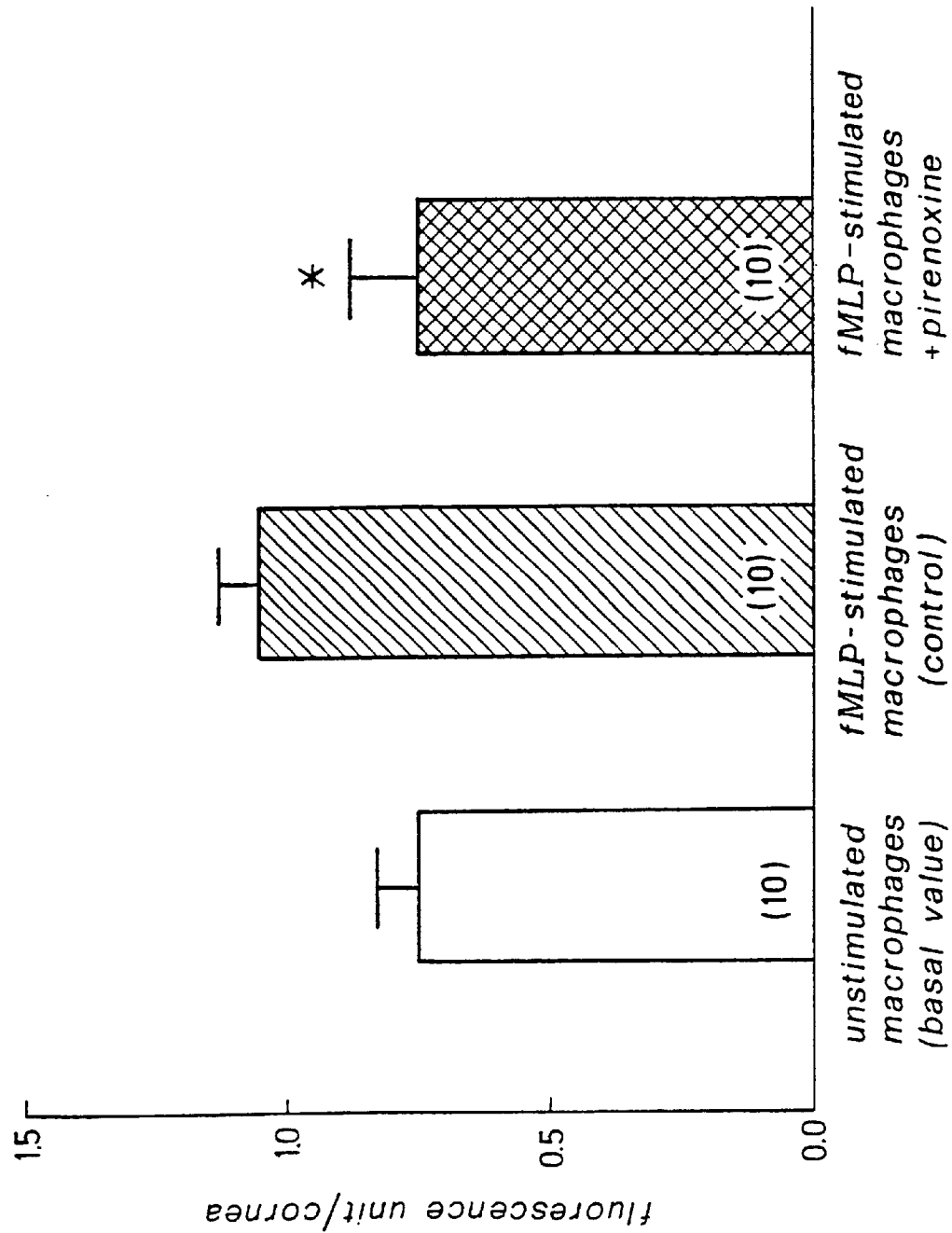

The present invention concerns the use of pirenoxine for the protection of the corneal tissues in photokeratectomy interventions. More particularly, the invention concerns the use of pirenoxine and salts thereof as agents able to inhibit within the cornea the oxidative phenomena determined by reactive oxygen species (or ROS, reactive oxygen species) which are produced in the tissues following the laser irradiation.

As known, the ophthalmic surgery, and particularly the refractive one, which aims to modify the eye refractive power in order to correct not negligible visual defects makes use of various, less or more consolidated or in evolution techniques, some examples of which are radial keratectomy, epikeratofachia and keratomileusis. In addition to these, also in the ophthalmology field the use of laser, particularly solid state laser, (like neodymium:yttrium-aluminiumrnarnet laser, known as Nd:YAG), and, above all, excimer laser, is remarkably increased.

Excimer laser is a pulse laser which, due to the decay of excited noble gas dimers (excimers obtained from gas mixtures of halogen and noble gases), are able to emit large amounts of energy in form of radiation within the range of far ultraviolet (UV-C), in the form of pulse trains having predetermined duration, frequency and fluence. Any photon emitted during the irradiation has enough energy to break the intramolecular bonds of the exposed material, in such a way that the irradiated molecules are "broken" in small volatile fragments which are expulsed at supersonic speed embodying a process known as "photodecomposition".

In the applications using the excimer laser in corneal surgery interventions usually an argon-fluorine laser, emitting radiation with a wavelength of 193 nm, which is suitable to carry out highly precise interventions with an optimal control on the penetration depth and a minimal thermal or mechanical damage effect on adjacent to exposed tissues, is usually employed. Contrary to other lasers used in clinical field, the excimer laser does not emit energy concentrated in a focal point but it has a radius with a large cross section which, going through suitable slits, is directed to strike large surface cornea zones with an accurate control of the shape and sizes of the exposed zones. The emitted energy is almost totally adsorbed by a surface layer within a thickness of few microns and results, by means of evaporation, in ablation at every pulse of cornea layers little more thicker than molecular, with a reproducibility not attainable by other techniques.

The excimer laser is widely used for corneal refractive re-modelling in techniques known as photorefractive keratectomy or PRK and LASIK (laser intrastromal keratomileusis), for the correction of various ametropias among which the most diffused is myopia. As known, the latter is a defect determined by a cornea curvature higher than required by the length of ocular bulb, so that light rays from outside are refracted in a such way that, before to reach the retina, they converge in a focal point. In this circumstance the use of excimer laser provides that layers of corneal tissue, the thickness of which is increasing toward the centre, be ablated reducing therefore the curvature of the cornea. When the technique is used for the correction of hypermetropia, wherein, on the contrary, the modification to be obtained is an increase of the cornea curvature, the amount of ablated tissue within the periphery of the exposed zone is more important than in the centre. Finally for the correction of the astigmatism which, as known, is an ametropia caused by curvature difference in various meridians of the ocular surface, the depth of the ablation can be asymmetric, depending on the meridian to be "flatted".

More recently the use of the excimer laser has been suggested for the therapeutic removal of surface corneal tissues, for the treatment of various corneal irregularities and opacities: like of dystrophic, degenerative, cicatricial or infective type. Such an operation, called phototherapeutic keratectomy or PTK, has been used, for example, for the treatment of recurrent corneal erosions, post-operation kerattis, corneal dystrophies as Reis-Buckler dystrophies, corneal opacities or cicatrices caused by Herpes simplex, surface irregularities following surgical interventions, for example as outcomes from keratoplasty or refractive corneal interventions. Contrary to refractive photokeratectomy PTK aims to eliminate irregularities on the corneal surface in order to flat the profile thereof and therefore involves the ablation of tissue layers with different thickness in the various zones of treated corneal surface.

Although the above described photokeratectomy interventions appear to be an alternative less traumatic than surgical ophthalmic techniques, the restorative process after the photoablation is not without drawbacks which are less or more transitory and boring or dis-enabling for the patient, among which, for example, there are corneal cicatricial problems, generation of under-epithelial opacities called "haze", which determine a reduction of visual efficiency resulting from "light scattering" phenomenon (light diffusion) and, in some circumstances, a reduction of refractive values as result of operation. It appears to be not debatable by those skilled in the field that at least partially such effects result from the formation of free radicals and, generally, reactive oxygen species, which was detected as side effect of UV irradiation and temperature increase occurring in the involved tissues.

As known the term "reactive oxygen species (or substances)", or ROS, presently collectively means the free radicals and not radical chemical species which currently take part into oxidative biological processes and whose excess with respect to the natural equilibrium conditions is considered to be the base of an ever increasing number of degenerative and pathological phenomena. Specifically the term ROS comprises superoxide anionic radical $O_2.$, hydroxyl radical $OH^-$, singlet oxygen $^1O_2$ and the hydrogen peroxide, $H_2O_2$, as well as alkoxide RO. and peroxide ROO. radicals which are generated from organic molecules during the oxidative processes. The activity of these species exerts, within the organism, on various cellular components, among which there are a large number of structural proteins and enzymes, DNA, RNA and, above all, the membrane lipids.

In fact the lipid peroxidation is the most known mechanism by which ROS exert their degenerative activity on the cellular structures damaging polyunsaturated fatty acids (PUFA) contained in the cytoplasmic membranes, often as phospholipid esters. In the initial step of this process the action of a free radical abstracts an hydrogen atom H. from the lipid chain, forming a free radical R* which undergoes a molecular rearrangement of the double bonds resulting in a conjugated diene radical. The latter rapidly reacts with molecular oxygen forming thus a lipid peroxide radical ROO., which, being a so strong oxidant to attack another PUFA, starts the propagation step of the reaction. In such a way a lipid hydroperoxide radical, ROOH; and, correspondingly, another lipid peroxide radical ROO., are formed. Therefore the above described main branch of the reaction occurs by means of radical chain attacks to the membrane lipids which are thus transformed step by step in the corresponding hydroperoxides till to the chain termination by means of a free radical.

Various agents naturally occurring in the cellular tissues can perform the above described action, practically functioning as scavengers or antoxidants. Among these the most known are C (ascorbic acid) and E (alpha tocopherol) vitamins, antioxidant enzymes as superoxide dismutase (SOD), catalase, gluthatione peroxidase and various low molecular weight compounds, among which gluthatione (GSH), tyrosine, uric acid. The natural protection from oxidative stresses performed by these substances, however, can not be enough strong to antagonize the degradation effect of ROS, in which circumstance the lipid peroxidation can result in an irreversible damage to the cellular membranes.

It has been also demonstrated that the oxidized forms of transition metal ions, as $Fe^{3+}$ and $Cu^{2+}$, in the presence of $H_2O_2$, can accelerate the oxidative mechanism by a non enzymatic reaction known as Fenton reaction. In the presence of a reducing agent, as ascorbate, part of the oxidized ions is reduced to the lower oxidation state (for example $Fe^{2+}$) and the reaction, whose rate depends on the $Fe^{3+}:Fe^{2+}$ ratio, proceeds, resulting in the conversion of hydrogen peroxide in hydroxyl ion, $OH^-$, plus an hydroxyl radical, OH. The latter represents the most reactive ROS.

Although it is difficult to detect ROS due their reactivity and therefore their short life times, the formation of free radicals in tissues subjected to photoablation using excimer laser has been widely demonstrated. For example the presence of free radicals in bovine corneas exposed to irradiation using ArF laser has been revealed by EPR spectroscopy (electron paramagnetic resonance) (R. J. Landry et al., Laser and Light in Ophthalmol., 6: 87–90, 1994), while measurements of temperature increase at level of the corneal endothelium and analytical determinations of the reduction of the SOD activity at level of the aqueous humour confirmed the formation of ROS in the cornea of PRK treated rabbits (K. Bigihan et al., Jpn. J. Ophthalmol., 40, 154–157, 1996). The lipid peroxidation has been detected, again in the rabbit cornea, following PTK treatment performed using excimer laser, both by histochemical test and the analytical detection of the presence of degradation products in corneal lipid extracts, particularly conjugated dienes and ketodienes (S. Hayashi et al., British J. Ophthalmol. 81, 141–144, 1997).

Further it has been pointed out by EPR spectroscopy the generation of free radicals also when corneal tissues are irradiated using solid state Nd:Yag laser, at a wavelength of 213 nm rather than 193 nm, which wavelength is typical of the argon-fluorine excimer laser. However in this case in addition to an oxidative damage comparable to that obtained using the excimer laser, it has been also detected a more remarkable cytotoxic effect, somehow dependent on the higher wavelength of the radiation (E. Edigeretal., Lasers Surg. Med., 21:88–93, 1997).

In addition to the effect of the UV radiation on the primary production of ROS, it has been also observed that the chemiotaxis activity of thus formed lipid hydroperoxides withdraws in situ polymorphonucleated cells and macrophages which in turn, by producing further ROS, enhance the damaging action of the radiation inducing a set of cytotoxic effects (H. Goto et al., Curr. Eye Res., 10:1009–1014, 1991).

Although the above reported literature demonstrates the formation of free radicals and reactive oxygen species in the photoablation treatment and relates this phenomenon to other possible post-operation complications it is not considered to be particularly important the protection of the corneal tissues by administration of exogenous agents having ROS antagonizing activity both before and after the operation. In effect the currently used pharmacological therapy for the photokeractectomy treatments is consisting of the topic ocular application, after the operation, of antibiotics, with the clear purpose to maintain in aseptic conditions the ocular surface during the cicatrization process, and anti-inflammatory drugs (steroidal or, according to the most recent trends, non steroidal) in order to act against the post-operation phlogosis conditions.

Therefore the object of the present invention is to provide the corneal tissues involved in UV irradiation, both before and soon after the treatment, with an agent suitable to perform a protective activity against the cellular damage triggered by the reactive oxygen species and to scavenge the action thereof. Particularly the suggested agent must be effective to oppose the lipid peroxidation in the corneal cellular tissues.

Within the studies about the effects of ROS and the inhibition of lipid peroxidation by various exogenous molecules having scavenging or antioxidant activity it has been found out that pirenoxine, an active principle already known and used therapeutically on another ocular district, the crystalline lens, shows a remarkable activity for the inhibition of lipid peroxidation in the comeal tissues and it is therefore able to perform a protective action against the cellular modifications resulting form laser irradiation.

Pirenoxine or 1-hydroxy-5-oxo-5H-pyrido-[3,2a]-phenoxazin-3-carboxylic acid (also called pirfenossone) is a known compound having the following formula:

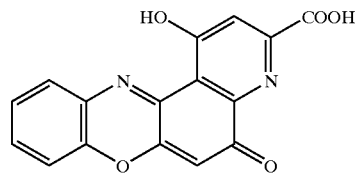

used in ophthalmology, usually in the form of sodium salt thereof, for the treatment of the cataract. The latter is an abnormal progressive condition of the eye crystalline lens characterized by an increasing loss of transparency. As known, the cataracts more often result from degenerative modifications, often occurring after 50 year age, while more rarely they can result from traumas or poison exposure. Initially the vision is hazy, then the brilliant lights dazzle diffusely and distortion and double vision can develop. At the end, if the cataract is not treated, anopia occurs. In addition to the surgical treatment, which becomes necessary for more advanced degenerative states and involves the ablation of the crystalline lens (with or without surgical implantation of an intraocular lens) the cataracts can be treated by the ophthalmic topic administration of pirenoxine in the form of collyrium.

It has been postulated that the ability of pirenoxine to inhibit the formation of lenticular opacities results from at least three different action mechanisms: (a) inhibition of the oxidation activity of the quinone molecules on the lenticular proteins, by binding their —SH groups; (b) activation and normalization of the cation pumping activity performed by the capsule of the crystalline lens; (c) inhibition of the sorbitol synthesis and reduction of the osmotic damage resulting from the storage of this substance (S. Iwata, J. Pharmac. Soc. Jap., 1964; 844: 435–440; F. Ikemoto et al., in: Proc. 50$^{th}$ Congr. Pharmacol. Soc. Jap., Kanto Region, 1974: I. Korte et al., Ophthalmic Res., 1979; 11: 123–125).

Within the most recent studies about the biological activity of pirenoxine it has been also found out, and it is the object of the european patent application No. EP 0885612, assigned to the present Applicant, that this molecule, in addition to the activity in the treatment of cataract, is has anti-inflammatory properties too. These properties, which have been verified on animal models, embody through an action mechanism not elucidated in the mentioned patent application, although in the above mentioned patent description it is postulated an inhibiting activity of the oxidative catabolism of arachidonic acid, which results in the production of prostaglandins.

According to the present invention it has been found out, as already reported, that pirenoxine can be advantageously used for the protection of the corneal tissues during excimer laser treatments because it is active in inhibiting the lipid peroxidation in the corneal cellular tissues.

It is therefore an object of the present invention the use of 1-hydroxy-5-oxo-5H-pyrido-[3,2a]-phenoxazin-3-carboxylic acid (pirenoxine) or a pharmaceutically acceptable salt thereof for the production of a topic ophthalmic drug suitable for the protection of the corneal tissues in photokeratectomy interventions. As already pointed out the suggested drug is designed as inhibitor of the ROS activity (reactive oxygen species) at level of corneal tissues and, particularly as inhibitor of the lipid peroxidation at level of said tissues.

Use of pirenoxine as pre- and post-operation protective agent finds application in any photokeratectomy treatment, being further presumable a wider use in those treatments which presently are more diffused, i.e. corneal photoablation by means excimer laser, both refractive and therapeutic and, in the first case by means of both PRK and LASIK technique.

The ophthalmic preparations of the present invention preferably contain the active principle, i.e. pirenoxine or a pharmaceutically acceptable salt thereof, in amount from 0,0001% to 0,01 weight %, expressed as free acid. More conveniently said medicaments contain from 0,001% to 0,005 weight % of pirenoxine, expressed as free acid, the optimum concentration being the same as that presently used for the therapy of the cataract, i.e. 0,005 weight %. Most conveniently said pirenoxine is in the form of the sodium salt. When used in the form of collyrium containing 0,005 weight % of the active principle, the preparation according to the invention can be administered, in order to obtain the desired effect of ROS inhibition, at a dosage of one-two drops twice or three times a day, preferably two drops three times a day, beginning at least one or two days before the operation and continuing, after the operation, over at least one or two days. Generally the dosage and posology can be widely variable without impairing the whole protective effect against ROSs exerted by the product.

The ophthalmic topic drug containing pirenoxine or a salt thereof can be, generally, in the same forms as prepared or proposable for the use of the same active principle for the therapy of the cataract or ophthalmic inflammation, as described in the above mentioned european patent publication EP-A-0885612. Particularly, the product can be in the form of aqueous solution or suspension for collyrium or in the form of emulsion, ointment, gel or cream. Preferably the product is administered as aqueous ophthalmic solution. Because of the instability of the active principle, pirenoxine is normally formulated, in the already used medicaments for the treatment of the cataract, as a two component preparation wherein a first component comprises freeze-dried pirenoxine and the second component comprises an eye acceptable aqueous carrier or diluent. The two components are reconstituted before the use and the thus obtained solution can be generally stored at ambient temperature for about two weeks without degradation.

Generally the compositions containing pirenoxine or a salt thereof according to the invention can be formulated according to the known art, for example according to the teachings suggested by "Remington's Pharmaceutical Sciences Handbook", Hack Publ. Co., U.S.A. Usually one or more agents for the regulation of tonicity should be added whereby the solution has a suitable osmolarity value. Any one of the products usually used in the art can be used, as, for example, sodium chloride, potassium chloride, mannitol, dextrose, boric acid, propylene glycol. The preparation can also comprise acids or bases as agents for the regulation of pH and/or buffers, as, for example, monosodium phosphate—disodium phosphate, sodium borate—boric acid or sodium succinate—succinic acid systems. For a good tolerability in the eye the pH should be between 4,5 and 8,5. Furthermore the composition should also comprise preservatives and antimicrobial agents, as benzalkonium chloride, sodium merthiolate or thimerosal, mehyl-, ethyl- and propylparaben, chlorobutanol, as well as chelating or sequestering agents as edetates or EDTA. If the product is packaged in unit dose containers the presence of preservatives can be avoided but, when multiple dose containers are used, for example vials for collyrium containing from 5 to 15 ml, the presence of the preservatives is necessary.

In addition the ophthalmic preparation can comprise further optional ingredients, as thickening agents, antioxidants, stabilizers, surface active agents, ecc. Only for exemplary purpose the composition of an already commercially available product designed for the treatment of the cataract is described below. The formulation can be suitable also for the use of the product as cornea protective agent against free radicals and ROS.

Figure 2:
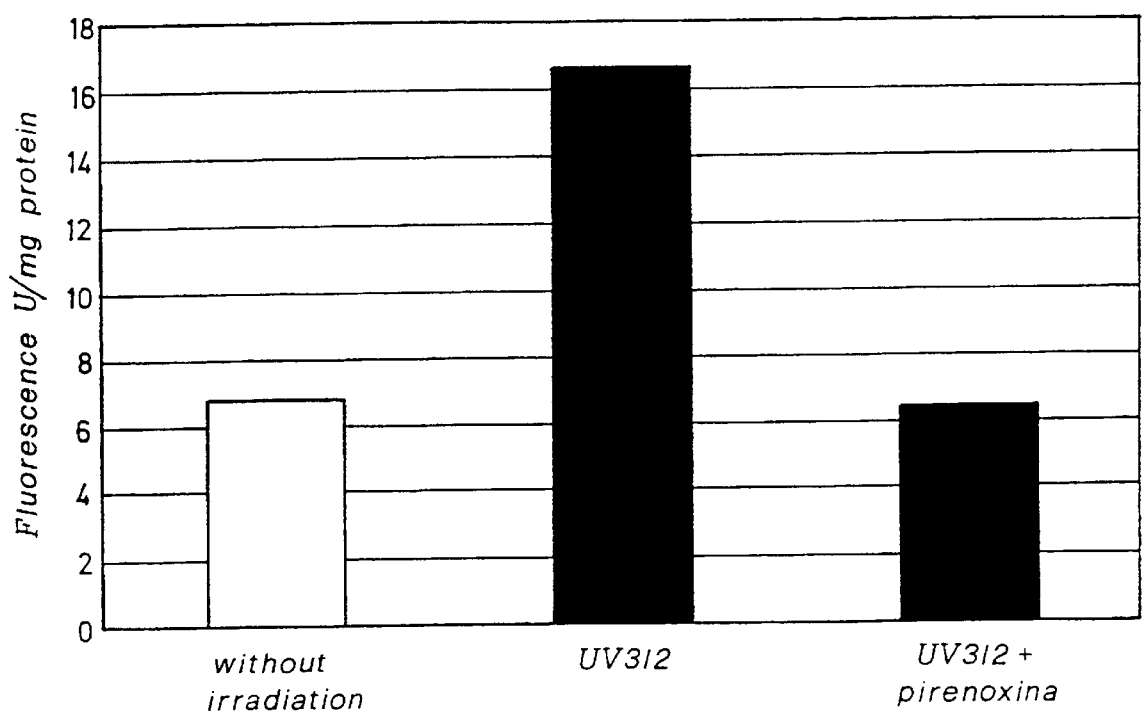
Figure 3:
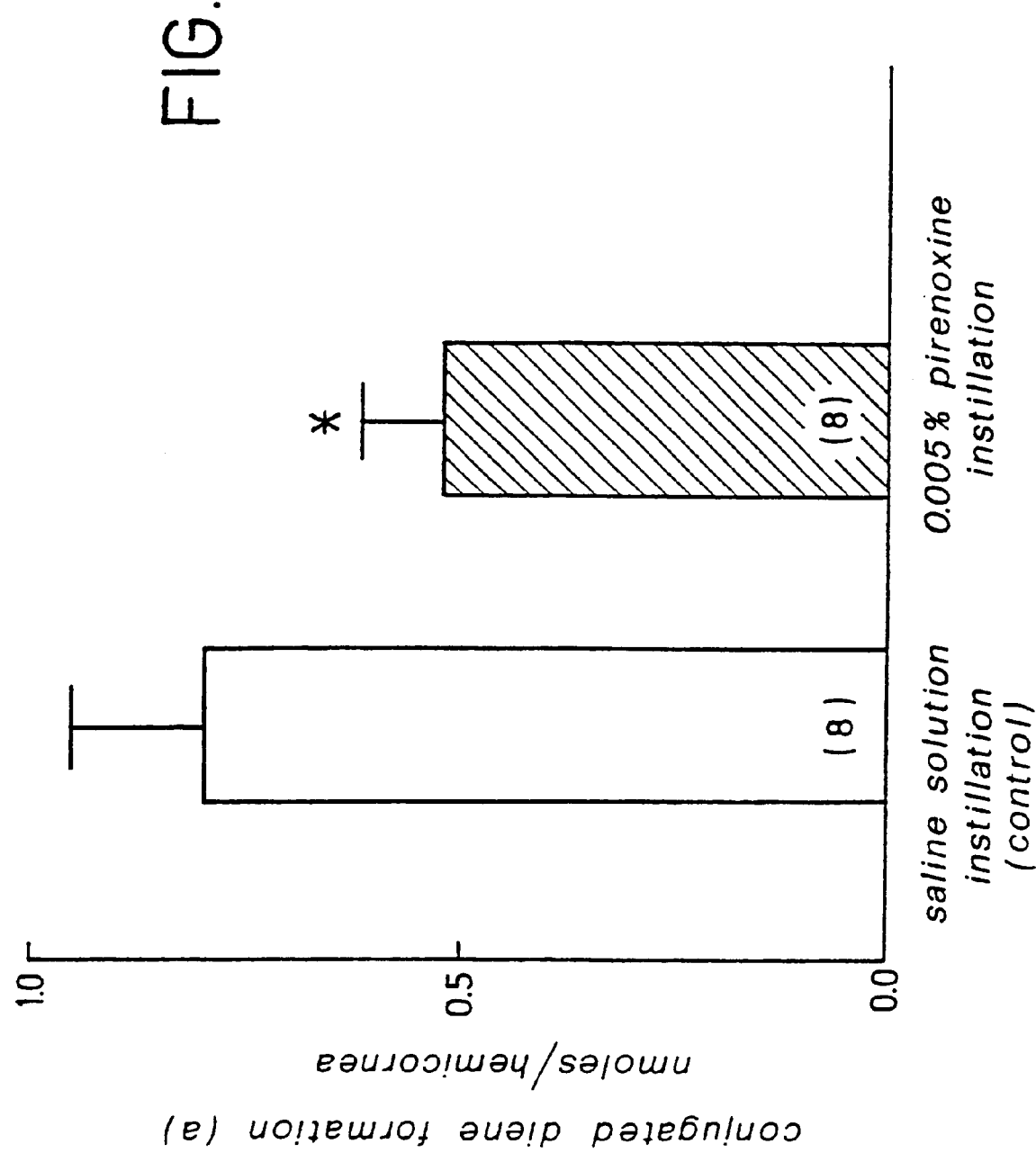

Some experimental results obtained within the scope of the present invention are reported below by way of example together with enclosed drawings, wherein:

FIG. 1 shows the effect of $10^{-5}$ M pirenoxine on fluorescence formation of lipidic soluble substances in rabbit corneas after incubation with f-MLP-stimulated autologous macrophages. Each bar±S.E.M. represents the mean value (in brackets the number of processed corneas). *: $p<0,01$ vs control. Control values are significantly higher than basal values ($p<0,0002$):

FIG. 2 shows the in vitro fluorescence formation of lipidic soluble substances in $UV_{312}$ irradiated (80 mJ/cm$^2$) epithelial corneal cells after incubation in presence and in absence of $10^{-5}$ M pirenoxine. The results are mean of 3 experiments;

FIG. 3 shows the ex vivo effects of pirenoxine instillations (60 μl every hour for 8 hours over 2 days) in the rabbit eyes on conjugated diene formation in the corneas in vitro submitted to iron-induced lipid peroxidation. Each bar±S.E.M. represents the mean value (in brackets the number of processed corneas). (a): expressed by difference between the sample and basal value (without iron-induction: 1.3±0,21 nmoles/hemicronea; n 0 8). *: $p<0,02$ vs control.

EXAMPLE

Formulation of Freeze-dried Sodium Pirenoxine

The dry powder component of the product has the following composition, wherein the amounts are given for the reconstitution in a 7 ml solution:

| | |
|---|---|
| sodium pirenoxine (equivalent to 0.350 mg of pirenoxine) | 0.376 mg |
| taurine | 34.34 mg |

In the preparation taurine and sodium pirenoxine are separately dissolved in deionized water, the two solutions are sterilized by filtration and then mixed together and subjected to the freeze-drying process.

| | |
|---|---|
| polyvinyl alcohol | 98 mg |
| succinic acid | 2.31 mg |
| sodium succinate .6$H_2$O | 89.215 mg |
| sodium chloride | 34.3 mg |
| benzalkonium chloride | 0.175 mg |
| sodium edetate | 0.89 mg |
| deionized water | q.b to 7 ml |

In addition to the ingredients mentioned in, the above description said formulation contains PVA as thickening agent The pH of the solvent component is 6. The formulation is prepared by firstly mixing and dissolving in water all the ingredients except benzalkonium chloride. After the complete dissolution of all the products benzalkonium chloride is added under continued stirring and the mixture is sterilized by filtration. The pH of the reconstituted product is 6–6.3.

Activity Tests as Inhibitor of the Lipid-peroxidation

In order to evaluate the performance of pirenoxine as protective agent against the action of ROS in the corneal tissues and particularly against the lipid peroxidation, the in vitro activity of pirenoxine both in corneal homogenates in presence of Fe(III)-ascorbic acid oxidizing system and on whole cornea subjected to the action of ROS generated from autologous macrophages was evaluated.

In addition the effects of the UV light on the cornea were carefully inspected because the comeal tissue is continuously exposed to the external environment and therefore to the combined action of oxygen and radiation.

The first experiments carried out by $UV_{312}$ irradiating corneal epithelial cells suggest that also in this case pirenoxine provides antioxidation protection.

The same molecule was assayed for its ex vivo action in the protection of the cornea against the oxidative in vitro attacks catalyzed by the presence of iron, as well as against the action of an iron physiological complex, ferritin, previously UV irradiated and then injected in the cornea stroma. In both case pirenoxine gave successful results.

From the experiments carried out up to now pirenoxine results to be an effective mean to protect the cornea affected from pathologies generated by reactive oxygen species.

In Vitro Effect of Pirenoxine on the Action of ROS Induced in Epithelium and Endothelium Homogenates of Rabbit Corneas The experimental procedure for the evaluation of the inhibiting action against the lipid-peroxidation exerted by pirenoxine in cornea epithelial and endothelial cells made use of Fe(III)-ascorbic acid system to induce the peroxidative phenomenon. The oxidative attack on membrane lipids was confirmed by the spectrophotometric determinations of both the conjugated dienes and fluorescent lipid-soluble substances which, as known, are generated by the oxidative degradation of lipid molecules.

Used experimental procedure included the following steps: a) abstraction of the cornea from the eye of male pigmented rabbits suitably selected and prepared for the study; b) incubation of the latter in 100 $\mu$M phosphate buffer, pH 7,5, in the presence of 1000 U collagenase and 5 $\mu$M $CaCl_2$ for 20 hours at 37° C.; c) centrifugation at 35000 rpm at 0° C. for 10 minutes and washings of the sediment with phosphate buffer; d) homogenization of the cellular sediment in 1 ml of buffer, pH 7,4 (10% w/v); e) incubation of a suitable homogenate aliquot with 10 $\mu$M $FeCl_3$ and ascorbic acid in phosphate buffer, pH 7,4, at 27° C. for 30 minutes in presence and in absence of $10^{-5}$ M pirenoxine; f) extraction of the lipid-soluble substances using chloroform/methanol mixture (2:1 v/v). The determination of the conjugated dienes contained in the lipid extract was carried out according to Buege et al. (Methods Enzymol., 52: 302–310, 1974), whereas the fluorescent lipid-soluble substances were determined according to Fletcher et al. (Anal. Biochem. 52: 1–2, 1973). The test results are reported in the table below.

TABLE 1

| | Conjugated dienes mmol/hemicornea | Fluorescence U/hemicornea |
|---|---|---|
| Homogenate (basal value) | 2.93 ± 0.14 | 4.91 ± 0.11 |
| Homogenate + Fe(III) (control) | 3.49 ± 0.13* | 5.89 ± 0.11# |
| Homogenate + Fe(III) + $10^5$ M pirenoxine | 2.77 ± 0.07* | 5.22 ± 0.13## |

Each value ± SEM represents the mean value of at least 3 (x2) determinations
*$p < 0.05$ and
: $p < 0.001$ vs relative basal values;
**: $p < 0.001$ and
: $p < 0.005$ vs relative controls.

From data reported in the above table it is apparent that pirenoxine exerts a clear inhibiting activity against the lipid-peroxidizing action of ROS, induced by Fe(III)-ascorbic acid system, as can be deduced from the remarkable decrease of the conjugated dienes and significant decrease of the fluorescent lipid-soluble substances when the above-said molecule was present.

In Vitro Protective Effect of Pirenoxine on Corneas Subjected to the Action from ROS Produced from f-MLP-stimulated Autologous Rabbit Macrophages In order to evaluate the inhibition exerted by pirenoxine against the oxidizing activity of macrophage produced ROS at level of the cornea, the following procedure was carried out: (a) broncho-alveolar washing of the rabbit to obtain the macrophages; (b) abstraction of the cornea from the rabbit eye; (c) incubation of the corneas with $10^{-7}$ M f-MLP stimulated or not stimulated macrophages (800000 cells/well) for two hours at 37° C., 5 % $CO_2$ in presence and in absence of $10^{-5}$ M pirenoxine; (d) separation and homogenization of the epithelial and endothelial corneal cells and subsequent determination of fluorescence as described in b, c, d and f steps of the above methodology.

The results reported in FIG. 1 show that by incubating the whole corneas together with autologous macrophages in the presence of pirenoxine the levels of the induced fluorescence result remarkably lower than the controls and are comparable to those of normal corneas (basal values).

In Vitro Protective Effect of Direnoxine on the Action of ROS Induced in UVB Irradiated Epithelial Cells The protective effect of pirenoxine on epithelial comeal cells (SIRC) irradiated for 36" using $UV_{312}$ light (80 mJ/cm$^2$), according to the following procedure: (a) the corneal cells were plated in 35 mm diameter wells; (b) at 80% confluency the cells were contacted with a medium at low (0,2%) serum content to inhibit the proliferation thereof during the experiment (c) the cells were irradiated with UV light in presence and in absence of 10$^{-5}$ pirenoxine, incubated at 37° C. for 17 hours and homogenized in 10 mM f) phosphate buffer, pH 7,4; (d) the lipid-soluble fluorescent substances and the proteins contained in suitable homogenate aliquots were determined.

The results reported in FIG. 2 and in table 2 show that pirenoxine exerts a protective effect. In fact the lipid-soluble fluorescent substances produced from epithelial corneal cells following the UV$_{312}$ irradiation and in presence of said molecule were notably lower (about two and half times) than those produced form cells irradiated in the same way but not protected by pirenoxine and show fluorescence values equal to those of not irradiated cells.

TABLE 2

|  | U/well | Proteins, mg/ml | U/mg protein |
| --- | --- | --- | --- |
| | Cells 17/12 | | |
| Control | 4.029 | 0.405 | 9.95 |
| UV312 | 7.3 | 0.27 | 27 |
| UV312 + pir. | 3.66 | 0.403 | 9.08 |
| | Cells 20/12 | | |
| Control | 1.61 | 0.171 | 9.4 |
| UV312 | 2.256 | 0.13 | 17.35 |
| UV312 + pir. | 1.8 | 0.245 | 7.35 |
| | Cells 14/01 | | |
| Control | 4.48 | 0.444 | 1.08 |
| UV312 | 1.02 | 0.189 | 5.4 |
| UV312 + pir. | 0.92 | 0.333 | 2.76 |
| Mean Control | 6.81 | | |
| UV$_{312}$ | 16.6 | | |
| UV$_{312}$ | 6.4 | | |

Ex Vivo Effect of Pirenoxine on Rabbit Corneas Subjected in Vitro to the Action of ROS Using the same Fe(III)-ascorbic acid system to induce the lipid-peroxidation as in the first described test, the protective action of pirenoxine has been evaluated ex vivo according to the following experimental procedure: a) the right eye of same type rabbits as in the previous test was topically treated every hour for 8 hours and over 2 days with 2 drops of 0,005% pirenoxine in 0,145 M NaCl (1 drop=30 µl, corresponding to about 1,5 µg), whereas the left eye was treated only with saline drops (60 µl); b) at the third day the rabbit was sacrificed by pentobarbital injection (100 mg/kg body weight); c) the corneas, abstracted (115–120 mg), were withdrawn and incubated in 100 µM phosphate buffer, pH 7,5, in the presence of 1000 U collagenase and 5 µM CaCl$_2$ for 20 hours at 37° C.; afterwards: (d) centrifugation at 3500 rpm at 0° C. for 10 minutes and washing of the sediment with phosphate buffer; (e) homogenization of cellular sediment in 1 ml of pH 7,5 buffer; (f) extraction with chloroform/methanol mixture and spectrophotometric determination of the conjugated dienes. The experimental results are reported in FIG. 3 ant in table 3 below:

TABLE 3

| | (conjugated dienes (mmol/hemicornea)) |
| --- | --- |
| eyes with saline instillation | 1.85 ± 0.31 |
| eyes with pirenoxine instillation | 1.34* ± 0.2 |

Each value ± SEM represents the mean of at least 3 (x2) determinations
*p < 0.05

The values reported in table 3 indicate that pirenoxine, administered topically in the rabbit eyes, reaches in the cornea such a concentration to in vitro contrast the lipid-peroxidizing action of ROS, in fact the formation of conjugated dienes in corneas of eyes (right) subjected to 0,005% pirenoxine instillation was lower than that present in eyes (left) treated only by saline.

In Vivo Effect of Pirenoxine on Rabbit Corneas Subjected to, Intrastroma Injection of UV Irradiated Ferritin The in vivo effect of pirenoxine was evaluated according to the following:

(a) rabbits were anaesthetized by low pentobarbital doses (20 mg/kg); (b) 25 µl of 50 µM ferritin in 0,15 M NaCl were injected in the stroma of the cornea by a 0,33×13 mm/29G insulin syringe whereas the controls were treated with 25 µl physiological solution; (c) in the eyes every hour two drops (1 drop=30 µl) of 0,005% pirenoxine in 0,145 M NaCl 8 times a day over 4 days were instilled, whereas the controls were treated only with the solvent, in the same amount and frequency; (d) at the 5$^{th}$ day the animals were sacrificed using a pentobarbital overdose (100 mg/kg); (e) the corneas were abstracted and the tissue cells separated and collected according to the procedure described in the ex vivo experiment; (f) the conjugated dienes and fluorescent soluble lipid contained in suitable homogenate aliquots were determined.

The obtained data, reported in table 4, point out a reduction of the lipid peroxidation in the corneas of pirenoxine treated eyes, as indicated by the decrease of conjugated dienes and fluorescent lipid soluble substances.

TABLE 4

| Eyes with ferritin intrastromal injection | Conjugated diene Nmoles/hemicornea | Fluorescence Unit/hemicornea |
| --- | --- | --- |
| Eyes with saline installation (without ferritin: basal value) | 1.6 | 4.5 |
| Eyes with saline installation (control) | 2.1 | 11.5 |
| Eyes with 0.005% pirelnoxine installation | 1.7 | 4.4 |

In vivo conjugated diene and lipid soluble fluorescence substance formation in corneas 5 days after the rabbit eyes were submitted to intrastromal injection of UV-irradiated ferritin and topical instillation of pirenoxine solution (2 drops every hour for 8 hr over 4 days)

The present invention was described with reference to some specific embodiments thereof but it is understood that modifications or variations can be carried out by those skilled in the art without departing from the scope thereof.

What is claimed is:

1. A method for the protection of corneal tissue in a photokeratectomy intervention comprising the administration onto the corneal tissue of a topical opthalmic drug comprising 1-hydroxy-5-oxo-5H-pyrido-phenoxazin-3-carboxylic acid (pirenoxine) or a pharmaceutically acceptable salt thereof.

2. The method of claim 1, wherein the topical opthalmic drug is an inhibitor of ROS action at the level of corneal tissues.

3. The method of claim 2, wherein the topical opthalmic drug is an inhibitor of the lipid peroxidation at the corneal level.

4. The method of claim 1, wherein the photokeratectomy intervention is a corneal photoblation intervention using an excimer laser.

5. The method of claim 1, wherein the topical opthalmic drug contains from 0.0001% to 0.01% by weight pirenoxine, expressed as free acid.

6. The method of claim 5, wherein the topical opthalmic drug contains from 0.001% to 0.005% by weight pirenoxine, expressed as free acid.

7. The method of claim 1, wherein the pirenoxine is in the form of the corresponding sodium salt.

8. The method of claim 1, wherein the topical opthalmic drug is in the form of an aqueous solution or suspension for collyrium or in the form of an emulsion, an ointment, a gel, or a cream.

9. The method of claim 8, wherein the aqueous solution is obtained by reconstitution of a two component preparation, wherein a first component comprises freeze-dried pirenoxine, in the form a sodium salt, together with an eye acceptable carrier, and the second component comprises an eye acceptable aqueous carrier or diluent.

* * * * *

UNITED STATES PATENT AND TRADEMARK OFFICE
CERTIFICATE OF CORRECTION

PATENT NO.    : 6,610,686 B1
DATED         : August 26, 2003
INVENTOR(S)   : Enrico Boldrini et al.

It is certified that error appears in the above-identified patent and that said Letters Patent is hereby corrected as shown below:

<u>Title page,</u>
Item [73], Assignee "Ausimont S.p.A. (Milan, IT)" should read -- Farmigea S.p.A. (Pisa, IT) --.

Signed and Sealed this

Twenty-first Day of October, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,610,686 B1 Page 1 of 1
DATED : August 26, 2003
INVENTOR(S) : Enrico Boldrini et al.

It is certified that error appears in the above-identified patent and that said Letters Patent is hereby corrected as shown below:

Title page, Item [54] and Column 1, line 2,
Title, delete "USE OF PIRENOXINE FOR THE PROTECTION OF CORNEAL TISSUES IN PHOTOKERACTOMY" and replace with -- USE OF PIRENOXINE FOR THE PROTECTION OF CORNEAL TISSUES IN PHOTOKERATECTOMY --

Title page,
Item [12], delete "Enrico et al." and replace with -- Boldrini et al. --.
Item [75], Inventors, delete "Boldrini Enrico, Pisa (IT); Ciuffi Mario, Florence (IT)" and replace with -- Enrico Boldrini, Pisa (IT); Mario Ciuffi, Firenze (IT) --

Signed and Sealed this

Thirtieth Day of November, 2004

JON W. DUDAS
*Director of the United States Patent and Trademark Office*